US009067041B2

(12) United States Patent
Watanabe et al.

(10) Patent No.: US 9,067,041 B2
(45) Date of Patent: Jun. 30, 2015

(54) MICROCATHETER

(75) Inventors: Masatoshi Watanabe, Bungoono (JP);
Koji Horikawa, Bungoono (JP)

(73) Assignee: KAWASUMI LABORATORIES, INC., Tokyo (JP)

(*) Notice: Subject to any disclaimer, the term of this patent is extended or adjusted under 35 U.S.C. 154(b) by 777 days.

(21) Appl. No.: 12/441,034

(22) PCT Filed: Sep. 13, 2006

(86) PCT No.: PCT/JP2006/318547
§ 371 (c)(1),
(2), (4) Date: May 12, 2009

(87) PCT Pub. No.: WO2008/032412
PCT Pub. Date: Mar. 20, 2008

(65) Prior Publication Data
US 2010/0036363 A1 Feb. 11, 2010

(51) Int. Cl.
*A61M 25/00* (2006.01)
(52) U.S. Cl.
CPC ....... *A61M 25/0045* (2013.01); *A61M 25/0054* (2013.01); *A61M 25/005* (2013.01); *A61M 25/0012* (2013.01); *A61M 2025/0042* (2013.01)
(58) Field of Classification Search
CPC .......... A61M 25/0054; A61M 25/005; A61M 25/0012; A61M 2025/0042
USPC .................................. 604/524–527
See application file for complete search history.

(56) References Cited

U.S. PATENT DOCUMENTS

| 5,358,493 A | 10/1994 | Schweich, Jr. et al. |
| 5,662,622 A | 9/1997 | Gore et al. |
| 5,851,203 A | 12/1998 | Van Muiden |
| 2002/0156460 A1* | 10/2002 | Ye et al. ................ 604/534 |
| 2003/0028173 A1 | 2/2003 | Forsberg |

FOREIGN PATENT DOCUMENTS

| JP | 58 188423 | 11/1983 |
| JP | 7 148264 | 6/1995 |
| JP | 2005 525133 | 8/2005 |

* cited by examiner

*Primary Examiner* — Emily Schmidt
(74) *Attorney, Agent, or Firm* — Oblon, McClelland, Maier & Neustadt, L.L.P.

(57) ABSTRACT

In a microcatheter, a shaft tube thereof is sectioned into a proximal zone, an intermediate zone, and a distal zone from a connector to the forward end thereof, each being formed of a multilayered tube, including three types of multilayered tubes different in hardness, an inner layer extending along all the zones from the proximal zone to the distal zone of the shaft tube, and a reinforcing material being fitted to the outer circumference of the inner layer, a first outer layer extending along all the zones from the proximal zone to the distal zone of the shaft tube so as to coat, and adhere to, the inner layer and the reinforcing material, to form a base layer structure of the inner layer/reinforcing material/first outer layer, a third outer layer coating the first outer layer of the base layer structure in the proximal zone, a second outer layer coating the first outer layer of the base layer structure in the intermediate zone.

14 Claims, 2 Drawing Sheets

MICROCATHETER

TECHNICAL FIELD

This invention relates to a microcatheter, and more specifically to a flexible microcatheter in which the hardness or flexibility continuously changes along or over nearly the entire length of the microcatheter.

The microcatheter of this invention not only has improved pressure resistance but also an antikinking property by embedding a braid into a plurality of flexible plastic layers different in hardness, and it is accordingly made possible for the microcatheter to approach or has a good access to minute blood vessel superselectively and it is also made possible for it to practice imaging of a blood vessel, administration of dosage, or treatment of embolus, etc., superselectively.

BACKGROUND ART

A microcatheter is a catheter that is used for injecting a medicament such as carcinostatic, or the like or a contrast medium (imaging agent) into a peripheral blood vessel of an organ such as a brain, a breast, an abdomen, or the like for practicing procedures such as the diagnosis, treatment, etc., thereof and that is made of an extra fine tube having a diameter of approximately 0.5 to 1.0 mm.

The above microcatheter to be used in a thin curved blood vessel passage is required to be extra fine and is also required to be highly flexible sufficient for inserting and passing it inside a lumen such as a curved blood vessel, etc., without damaging or impairing the blood vessel. On the other hand, since a flexible extra fine microcatheter is easily twisted in a passage having a very small radius, which causes a problem wherein a flow in a lumen may be limited or stemmed. Further, when a microcatheter is moved forward along a passage in a lumen or is made to transmit a torque, the above microcatheter with such an extra fine configuration is not structurally stable, causing a problem that the tube is bent or twisted at various sites along the entire length of the catheter.

For coping with the above problem, for example, PCT Japanese Translation Version 2003-501160 (Patent Document 1) proposes a microcatheter which has, as recited in claims 3 and 4 thereof, (a) an integral tube formed of an inside layer made of materials such as a polyether copolymer, a polyamide copolymer, a fluorine resin, etc., (b) a braid of stainless steel wire formed on the above inside layer for imparting resistance to twisting or preventing the conversion to an elliptical form and further for improving the degree of torque transmission and (c) an outside layer formed of a material comprising a mixture of polyamides as a base material or comprising a polyether and a polyamide as a base material, one of these being a material having a Shore hardness of 70 to 80D, the other being a material having a Shore hardness of 25 to 35D, a distal end portion having a Shore hardness of 25 to 35D, an intermediate portion having a Shore hardness of 25 to 80D and a proximal end portion having a Shore hardness of 70 to 80D, the above outside layer being a layer formed by extrusion of a mixture or formulated material of two materials different in hardness, the compositional ratio of the above two materials being changed during the extrusion so that the hardness of the above integral tube changes along the longitudinal direction.

In the invention of Patent Document I, however, only the hardness is changed without changing the outer dimensions of a shaft tube as shown, for example, in FIGS. 1 to 3. When the forward end diameter of the catheter is decreased, therefore, the diameter of that on the near end side at hand is too small, and even if the hardness of the resin is increased, the tube has only insufficient rigidity. On the other hand, when the diameter on the near end side at hand is increased, the forward end of the catheter is too large, thus involving a problem that the selectivity to a blood vessel is degraded. Further, since the outer layer tube is not continuously coated with same one material and one layer from the end portion near at hand through the forward end portion, there caused a problem that the adhesion to the braid is poor and that the catheter is inferior in pressure resistance and torque performance.

It is an essential basic structural requisite in microcatheter design that the microcatheter has a thin forward end portion (to be also referred to as "distal zone") and a large base end portion (to be also referred to as "proximal zone"). It is practically difficult to materialize any microcatheter of which the hardness alone is changed without changing outer dimensions of a shaft tube as described in Patent Document 1, and in reality such has not yet been commercialized.

Further, JP 2001-190681A (Patent Document 2) proposes a microcatheter having a catheter body having an inner layer and an outer layer as specified in claim 1 thereof, said outer layer having a first region and a second region that is positioned nearer to the base end side than the first region, said first region being constituted of a polyester elastomer, said second region being composed of a polyurethane elastomer having higher hardness than the polyester elastomer constituting said first region.

In the microcatheter described in Patent Document 2, however, the inner layer is coated with the outer layer formed of two layers, but the innermost layer (first outer layer) of the outer layer is not fully extended up to the forward end of a shaft tube. That is, it is constitutionally cut off in the middle of the shaft tube, so that the problem with the catheter is that the adhesion to a braid is poor and that the microcatheter is inferior in pressure resistance and torque performance.

Further, Japanese Patent No. 2865428 (Patent Document 3) in claim 1 and FIG. 10 and Japanese Patent 2965940 (Patent Document 4) in claim 1 and FIG. 7 describe microcatheters each having a catheter section having a long and narrow tubular member having a proximal end, a distal end and a passage that defines an inside lumen extending between the proximal end and the distal end; the catheter section having (a) a braid member that is a braid of a plurality of ribbons and that is only one reinforcing member having an inside surface and an outside surface, at least most of said ribbons containing an ultra-elastomeric alloy and said braid member extending along at least part of said lumen, (b) at least one polymeric inside lining member inside said braid member, and (c) at least one outside cover member outside said braid member.

However, in the microcatheters described in Patent Document 3 and Patent Document 4, the inner layer formed of two layers is coated with the outer layer formed of two layers, and yet the inner layer (first outer layer) of the outer layer is not fully extended up to the forward end of the shaft tube, either, that is, it is cut off in the middle of the shaft tube, so that, oppositely, the outer layer (second outer layer) of the outer layer is constitutionally extended up to the forward end of the shaft tube. Therefore, these microcatheters have problems similar to those in Patent Document 2.

It is therefore an object of this invention to provide a microcatheter that overcomes the problems of conventional microcatheters having poor adhesion between an outer layer tube and a braid, and being inferior in pressure resistance and torque performance, and that not only improves the pressure resistance of the catheter but also anti-kinking property, thereby making superselective good approach or access of the catheter to a minute blood vessel possible, and also enabling superselective imaging of a blood vessel, administration of dosage and treatment of embolus.

DISCLOSURE OF INVENTION

According to this invention, there are provided the following microcatheters.

1. A microcatheter 1 having a flexible shaft tube connected to a connector, said shaft tube 2 being sectioned into a proximal zone 3, an intermediate zone 4 and a distal zone 5 in this order in the longitudinal direction from said connector to the forward end thereof, each zone being formed of a multilayered tube, and said shaft tube (2) consisting of three types of multilayered tubes different in hardness, which comprises:

(i) an inner layer 8 extending along all the zones from the proximal zone 3 to the distal zone 5 of said shaft tube 2, and a reinforcing material 7 being fitted to the outer circumference of said inner layer 8, a first outer layer 11 extending along all the zones from the proximal zone 3 to the distal zone 5 of said shaft tube 2 so as to coat or cover and adhere to said inner layer 8 and said reinforcing material 7, to form a basic layer structure composed of the inner layer 8/reinforcing material 7/first outer layer 11, (ii) a third outer layer 13 coating the first outer layer 11 of said base layer structure in the proximal zone 3 of said shaft tube 2, and (iii) a second outer layer 12 coating the first outer layer 11 of said basic layer structure in the intermediate zone 4 of said shaft tube 2.

2. A microcatheter 1 having a flexible shaft tube connected to a connector, said shaft tube 2 being sectioned into a proximal zone 3, an intermediate zone 4 and a distal zone 5 in this order in the longitudinal direction from said connector to the forward end thereof, each zone being formed of a multilayered tube, and said shaft tube (2) consisting of three types of multilayered tubes different in hardness, which comprises:

(i) said proximal zone 3 being composed of an inner layer 8 and an outer layer 10 formed on the outer circumference thereof and composed of a plurality of layers having high hardness, said inner layer 8 having a reinforcing material 7 fitted to the outer circumference thereof, said reinforcing material 7 having said outer layer 10 composed of a plurality of layers coated on the outer circumference thereof, said outer layer 10 being composed of a plurality of layers being composed of an inner layer 11 (first outer layer 11) and an outer layer 13 (third outer layer 13), said inner layer 11 (first outer layer 11) coating on the outer circumference of said reinforcing material 7, and the outer layer 13 (third outer layer 13) coating the outer circumference of said inner layer 11 (first outer layer 11), (ii) said intermediate zone 4 being composed of the inner layer 8 and an outer layer 10' composed of a plurality of layers having intermediate hardness, said inner layer 8 having the reinforcing material 7 fitted to the outer circumference thereof, the outer layer 10' coating on the outer circumference of said reinforcing material 7, said outer layer 10' composed of a plurality of layers being composed of the inner layer 11 (first outer layer 11) and an outer layer 12 (second outer layer 12), the inner layer 11 (first outer layer 11) coating the outer circumference of said reinforcing material 7, the outer layer 12 (second outer layer 12) coating the outer circumference of said inner layer 11 (first outer layer 11), (iii) said distal zone 5 being composed of the inner layer 8 and an outer layer 10", said inner layer 8 having the reinforcing material 7 fitted to the outer circumference thereof, the outer layer 10" coating the outer circumference of said reinforcing material 7, said outer layer 10" being composed of the first outer layer 11 alone, and said first outer layer 11 coating said reinforcing material 7 and said inner layer 8 so as to extend along all of the proximal zone 3 to the distal zone 5 of the shaft tube 2, to form a base outer layer 11, and said base outer layer 11 having a basic layer structure extending so as to adhere to said reinforcing material 7 and said inner layer 8.

3. The microcatheter 1 recited in the above 1 or 2, wherein the outer layer 11 forming said base outer layer has a thickness of 0.03 mm or less.

In Figures, 1 indicates a microcatheter, 2 indicates a shaft tube, 3 indicates a proximal zone, 4 indicates an intermediate zone, 5 indicates a distal zone, 6 indicates a front chip, 7 indicates a reinforcing material (braid), 8 indicates an inner layer, 10, 10' and 10" indicate outer layers, 11 indicates a first outer layer (inner layer), 12 indicates a second outer layer (intermediate layer), 13 indicates a third outer layer (outer layer), 18 indicates an imaging marker, 19 indicates a connector, and 20 indicates a connector cover.

BEST MODE FOR CARRYING OUT THE INVENTION

Figure 1:
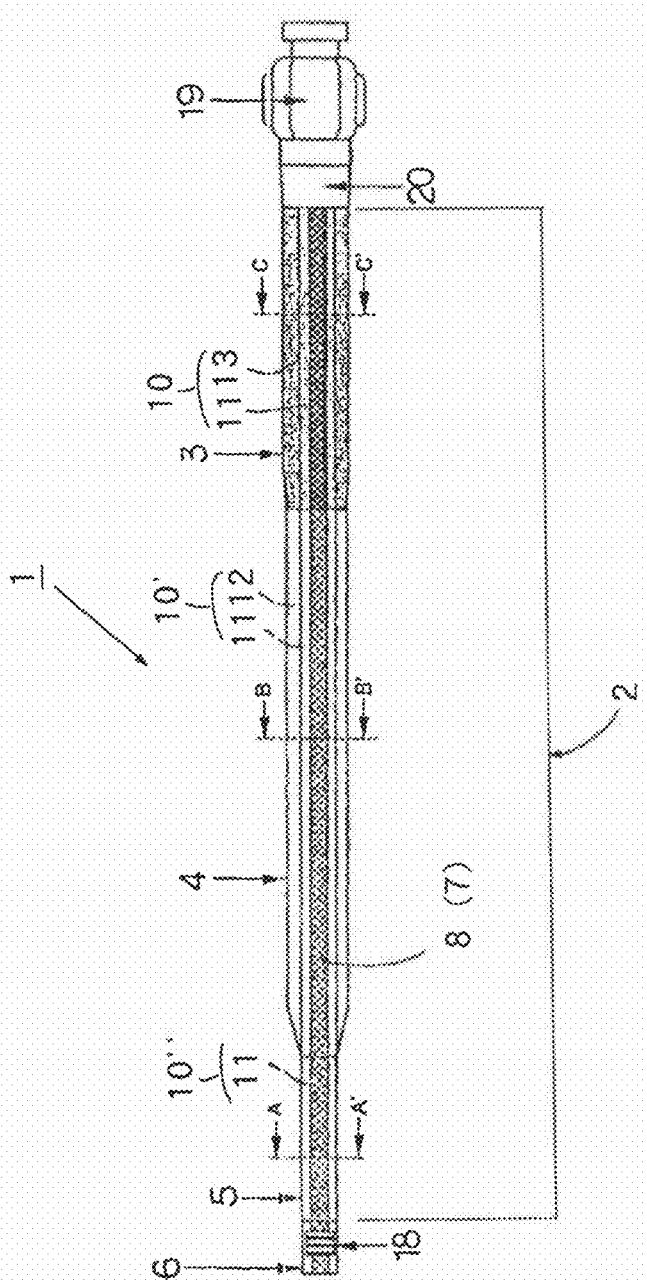
FIG. 1 is a schematic drawing for explaining the microcatheter of this invention.
Figure 2:
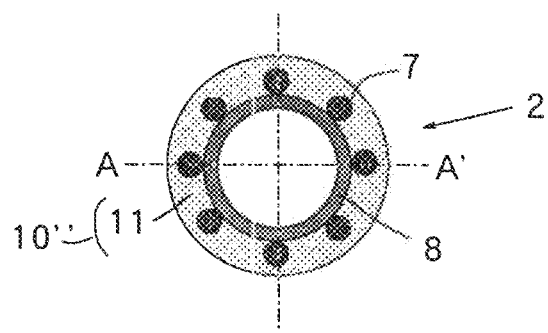
FIG. 2 is a cross-sectional view taken along A-A' in FIG. 1.
Figure 3:
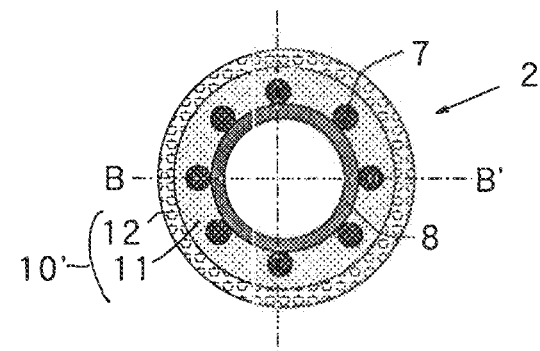
FIG. 3 is a cross-sectional view taken along B-B' in FIG. 1.
Figure 4:
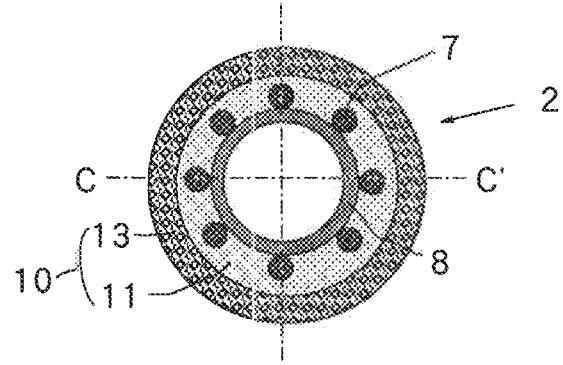
FIG. 4 is a cross-sectional view taken along C-C' in FIG. 1.

The best mode for practicing this invention will be explained in detail below with reference to drawings. (Constitution or configuration of shaft tube as a whole) In this invention, in a microcatheter 1 having a flexible shaft tube 2 connected to a connector 19 as shown in the schematic drawing of FIG. 1, the above shaft tube 2 extends in its forward end direction from the above connector 19 and is sectioned into a proximal zone (base end zone) 3, an intermediate zone 4 and a distal zone (forward end zone) 5, and each zone of these is formed of a multi-layered tube, and thus shaft tube (2) consisting of three types of multilayered tubes different in hardness. And, as shown in FIGS. 2 to 4, (i) an inner layer 8 is extended along or over all the zones of the shaft tube 2 from the proximal zone 3 (FIG. 4) through the intermediate zone 4 (FIG. 3) to the distal zone (5) (FIG. 2), and a reinforcing material 7 is fitted to the outer circumference of the above inner layer 8.

Further, a first outer layer 11 is extended along or over all of zones of the above shaft tube, from the proximal zone 3 to the distal zone 5 of the above shaft tube 2 so as to coat or cover and adhere to the above inner layer 8 and the above reinforcing material 7, to form a basic layer structure M composed of the inner layer 8/reinforcing material 7/first outer layer 11 which layer structure M is in common to all of the zones (at the distal zone 5 (FIG. 2), the first outer layer 11 corresponds to the outer layer 10").

Further, (ii) the proximal zone 3 (FIG. 4) of the above shaft tube 2 is provided with a constitution in which the first outer layer 11 of the above basic layer structure is coated or covered with a third outer layer 13 (outer layer 10 composed of a plurality of layers).

Meanwhile, (iii) the intermediate zone 4 (FIG. 3) of the above shaft tube 2 is provided with a constitution in which the first outer layer 11 of the above basic layer structure M, is coated or shrouded with a second outer layer 12 (outer layer 10' composed of a plurality of layers).

The constitution of each zone will be explained below.

(Proximal Zone 3)

The proximal zone 3 (base end portion) 3 is, in general, constituted of the inner layer 8 and the outer layer 10 composed of a plurality of layers having high hardness, formed on the outer circumference of the inner layer 8 as shown in FIG. 4. The inner layer 8 has the reinforcing material 7 fitted to the outer circumference thereof, and the outer circumference of the above reinforcing material 7 is coated or shrouded with the above outer layer 10 composed of a plurality of layers.

As shown in FIG. 4, the outer layer 10 is composed of the inner layer 11 (to be also referred to as "first outer layer 11"), and the outer layer 13 (to be also referred to as "third outer layer 13"), wherein the above inner layer 11 (first outer layer 11) is coated on the outer circumference of the above reinforcing material 7, and the outer circumference of the above inner layer 11 (first outer layer 11) is coated with the outer layer 13 (third outer layer 13).

The material for the inner layer 8 is selected, but not specially limited, for example, from polyolefins such as polyethylene (PE), polypropylene (PP), etc., and fluorine resins that have low frictional resistance and are chemically stable, such as PTFE (polytetrafluoroethylene), an ethylene/tetrafluoroethylene copolymer (ETFE), a tetrafluoroethylene/hexafluoropropylene copolymer (FEP), polychlorotrifluoroethylene (PCTFE), a tetrafluoroethylene/perfluoroalkylvinyl ether copolymer (PFE), polyvinylidene fluoride (PVDF), etc.

The resin for the inner layer 11 (first outer layer 11) constituting the outer layer 10 is preferably selected from those which are of a relatively soft grade and have good adhesion to a stainless steel braid, etc., constituting the reinforcing material 7, i.e., polyolefins such as polyethylene (PE), polypropylene (PP), etc., polyamides such as nylon 6, nylon 6,6, nylon 12, etc., a polyamide elastomer, a polyether block amide, a polystyrene elastomer, a silicone elastomer, etc. The resin for the outer layer 13 (third outer layer 13) includes polyolefins such as polyethylene (PE), polypropylene (PP), etc., polyamides such as nylon 6, nylon 6,6, nylon 12, etc., a polyamide elastomer, a polystyrene elastomer, a silicone elastomer, etc., and of these, those which are of a relatively hard grade and have good adhesion to the inner layer 11 are used.

As the reinforcing material 7, further, there are used a braid, a ribbon, a coil, etc., each of which is made from a metal wire such as stainless steel wire (stainless steel braid) (a wire having a size of approximately 50 to 30 µm), a synthetic resin (polyamide, polyethylene terephthalate, polybutylene terephthalate, etc.) or a carbon fiber.

(Intermediate Zone)

As shown in FIG. 3, the above intermediate zone 4 is constituted of the inner layer 8 and the outer layer 10' composed of a plurality of layers having an intermediate hardness. The reinforcing material 7 such as a braid made of the above metal, synthetic resin, or the like is fitted to the outer circumference of the above inner layer 8, and the above reinforcing material 7 has the outer layer 10', composed of a plurality of layers, coated or covered on the outer circumference thereof. The above outer layer 10' composed of a plurality of layers is constituted of the inner layer 11 (first outer layer 11) and the outer layer 12 (second outer layer 12), and the inner layer 11 (first outer layer 11) is coated or put on the outer circumference of the above reinforcing material 7. Further, the above inner layer 11 (first outer layer 11) has the outer layer 12 (to be also referred to as "second outer layer 12") coated on the outer circumference thereof.

The resin for constituting the outer layer 12 (second outer layer) includes, for example, polyamides such as nylon 6, nylon 6,6, nylon 12, etc., a polyamide elastomer, a polystyrene elastomer, a polyester elastomer, polyethylene (PE), polypropylene (PP), polyurethane, polyurethane elastomer, etc., and of these, those which are of a relatively soft grade are used.

(Distal Zone)

As shown in FIG. 2, the above distal zone (forward end portion) 5 is constituted of the inner layer 8 and the outer layer 10", and the reinforcing material 7 such as a braid made of a metal or synthetic resin, etc., is fitted to the outer circumference of the above inner layer 8. The outer layer 11 is coated on the outer circumference of the above reinforcing material 7, and in this case, the above outer layer 10" is constituted of the first outer layer 11 alone.

On the forward end of the above distal zone 5, a soft front chip 6 formed of an elastomer such as a polyamide elastomer is mounted, and an imaging marker 18 made, for example, of a platinum-iridium alloy, etc., as will be described later is fitted to the backward end of the front chip 6 (see FIG. 1). When a metal wire is used as an imaging marker 18, a coil made of a flat type wire (with flat cross sectional wire) or round type wire (round cross sectional wire) is used.

(Specific Features of Shaft Tube 2)

The microcatheter of this invention has a basic layer structure in which the above first outer layer 11 forms the base outer layer 11 by coating the above reinforcing material 7 and the above inner layer 8 over all zones of the shaft tube 2 from the proximal zone 3 to the distal zone 5, and this base outer layer 11 extends so as to adhere to the above reinforcing material 7 and the above inner layer 8. In the shaft tube of this invention, the first outer layer 11, in common, coats or covers the reinforcing material 7 and the inner layer 8 in the entire portion of the shaft tube 2 from the base end portion to the forward end portion as shown in FIGS. 1 to 4, so that the microcatheter of this invention can be improved in pressure resistance. That is, the inner layer 8/reinforcing material 7/first outer layer 11 constitutes the basic layer structure.

On the basis of the second outer layer 12 of the intermediate portion 4 and the third outer layer 13 of the base end portion, its hardness, diameter and length of the material (resin) are changeable. Thus, by changing or adjusting its hardness etc., the hardness (flexibility and balance) and flexural strength of the shaft tube 2 as a whole are changeable as desired.

The relationship of the first outer layer 11, the second outer layer 12 at the intermediate portion and the third outer layer 13 at the base end portion in terms of hardness may be in the order of the first outer layer 11<second outer layer 12<third outer layer 13 or the first outer layer 11<second outer layer 12=third outer layer 13 or the first outer layer 11<second outer layer 12>third outer layer 13 as shown in Examples to be described later. Further, since the first outer layer 11 common to the structure from the forward end portion to the base end portion, the second outer layer 12 at the intermediate portion and the third outer layer 13 at the base end portion can be formed from materials that are different in hardness alone but that have chemically identical qualities, there by they are excellent in adhesion.

Concerning Shore hardness of the multilayered tube constituting zones from the forward end portion (distal zone 5) to the base end portion (proximal zone 3), it is generally preferred to select a Shore hardness in the range of approximately 20 to 70 D for the forward end portion, a Shore hardness in the range of approximately 20 to 80 D for the intermediate portion and a Shore hardness in the range of approximately 50 to 90 D for the backward end portion as required. Concerning Shore hardness of each outer layer in each position, it is preferred to select a Shore hardness in the range of 25 to 55 D for the first outer layer 11 (distal zone), a Shore hardness in the range of 25 to 80 D for the second outer layer (intermediate zone 4) and a Shore hardness in the range of 70 to 80 D for the third outer layer 13 (proximal zone 3) as required.

(Tube Diameter)

In the microcatheter, the forward end portion (proximal zone 5) generally has a outer diameter of 2.1 Fr (0.70 mm) to 2.3 Fr (0.76 mm), and the microcatheter with such a small diameter is used, the first outer layer 11 is preferably formed to have a thickness of 0.03 mm or less. When the above thickness exceeds 0.03 mm, not only the outer diameter of the forward end portion (proximal zone 5) is too large, but also the flexibility of the forward end portion is impaired.

(Materials for Tube)

Resin materials for constituting the multilayered tube will be summarized below. For the first outer layer 11, the second outer layer 12 and the connector cover, there are used polyamides such as nylon 6, nylon 6,6, nylon 12, etc., a polyamide elastomer, a polystyrene elastomer, a polyester elastomer, polyethylene (PE), polypropylene (PP), polyurethane, a polyurethane elastomer, polyethylene terephthalate, polybutylene terephthalate, etc.

For the third outer layer 13, polyamides such as nylon 6, nylon 6,6, nylon 12, etc., a polyamide elastomer, etc., are used.

For each tube (proximal zone 3, intermediate zone 4 and distal zone 5), it is desirable to use the same resin for improving the adhesion.

(Production of Multilayered Tube)

The method of producing the multilayered tube in this invention is not specially limited. Most typically, first, a tube as the inner layer 8 is coated with the reinforcing material 7 that is, for example, a braid of a metal wire such as a stainless steel wire (stainless steel braid), to prepare a reinforcing-material-coated inner layer 8(7).

The thus prepared reinforcing-material-coated inner layer 8(7) is multilayer-coated by extruding the above reinforcing-material-coated inner layer 8(7) through a die of an extruder and melt-extruding resins for forming the first outer layer 11, the second outer layer 12 and the third outer layer 13 with an extruder having a multilayer ring die or with a plurality of extruders (3 extruders in this case). Thus, the reinforcing-material-coated inner layer 8(7) is coated or shrouded with the formation of the first outer layer 11, the second outer layer 12 and the third outer layer 13 by melt-extrusion molding, the adhesion between the inner layer and the first outer layer, the adhesion between the first outer layer and the second outer layer and the adhesion between the second outer layer and the third outer layer can be improved.

In place of the multilayer co-extrusion molding, naturally, multi-layer coating may be carried out by consecutive molding means in which while the reinforcing-material-coated inner layer 8(7) is extruded through the ring die of the extruder, the first outer layer 11 is coated or formed thereon first, then, while the reinforcing-material-coated inner layer 8 coated with the first outer layer 11 is extruded through a die of an extruder, the second outer layer 12 is coated or formed thereon, and similarly, the third outer layer 13 is formed.

Further, while the above reinforcing-material-coated inner layer 8(7) is extruded through the die of the above extruder, there may be carried out a consecutive extrude-laminating to form multi-layers thereon.

(Contrast Medium, etc.)

For practicing a more appropriate or precise operation while extracorporeally monitoring the state of the microcatheter in a lumen with X-ray, preferably, a contrast medium (imaging agent) is added to the front chip 6, the first outer layer 11, the second outer layer 12 and the third outer layer 13. For example, an imaging marker 18 is also formed on the forward end of the chip. The contrast medium is selected from known media, and for example, barium sulfate, tungsten, platinum, iridium, a platinum-iridium alloy, gold, etc., can be suitably applied.

Further, as required, a lubricant (e.g., polyvinyl pyrrolidone) may be coated on the outer circumferences of the front chip 6 toward some intermediate place of the third outer layer 13, through the first outer layer 11 and the second outer layer 12.

(Advantageous Effects of the Invention)

The microcatheter of this invention is improved in pressure resistance and also improved in anti-kinking property, so that when the microcatheter of this invention is used, it is made possible to have a good approach or access to a minute blood vessel superselectively, and it is hence made possible to practice imaging of a blood vessel, administration of dosage, or treatment of embolus, etc., superselectively.

EXAMPLES

Specific embodiments of this invention will be explained with reference to Examples hereinafter. In the following Examples, the hardness of each of inner layers and outer layers are shown as "Shore D hardness" measured with a Shore D hardness tester.

Comparative Example 1

(1) A shaft tube 2 that was formed of a multilayered tube for a microcatheter and that had a layer structure shown in Table 1 was produced as follows.

Sixteen stainless steel wires having a diameter of 0.03 mm each were braided on a PE tube that was employed for an inner layer 8 and that had a resin thickness of 0.015 mm and an internal diameter of 0.56 mm, to coat the outer surface thereof. A first outer layer 11, a second outer layer 12 and a third outer layer 13 were formed thereon by a simultaneous multilayer melt-extrusion with a multilayer extrusion molding machine having a ring die.

A polyamide elastomer (hardness 55 D) was used as a resin for the first outer layer 11, a polyamide elastomer (hardness 63 D), as a resin for the second outer layer 12, and a polyamide elastomer (hardness 77 D), as a resin for the third outer layer 13. The shaft tube 2 having a distal zone 5 with an outer diameter of 0.73 mm, an intermediate zone 4 with an outer diameter of 0.93 mm and a proximal zone 3 with an outer diameter of 0.93 was accordingly produced.

In the constitution of shaft tube 2, the polyamide elastomer as a resin for the first outer layer 11 was used for coating or covering the distal zone 5 alone.

(2) The above shaft tube was connected to a power injector, and a saline solution was injected to evaluate the shaft tube for its injection-admissible maximum pressure $P_{max}$ (psi(lb/in$^2$)) and a flow rate $FR_{max}$ (ml/sec.). A set injection speed of 10 ml/second and a set injection amount of 10 ml were employed. Table 2 shows the results.

Example 1

A shaft tube 2 that was formed of a multilayered tube for a microcatheter and that had a layer structure shown in Table 1 was produced as follows.

Sixteen stainless steel wires having a diameter of 0.03 mm each were braided on a PE tube that was employed for an inner layer 8 and that had a resin thickness of 0.015 mm and an internal diameter of 0.56 mm, to coat or cover the outer surface thereof. A first outer layer 11, a second outer layer 12 and a third outer layer 13 were formed thereon by a simultaneous multilayer melt-extrusion with a multilayer extrusion molding machine having a ring die.

A polyamide elastomer (hardness 55 D) was used as a resin for the first outer layer 11, a polyamide elastomer (hardness 63 D), as a resin for the second outer layer 12, and a polyamide elastomer (hardness 77 D), as a resin for the third outer layer 13. The shaft tube 2 having a distal zone 5 with an outer diameter of 0.73 mm, an intermediate zone 4 with an outer diameter of 0.93 mm and a proximal zone 3 with an outer diameter of 0.93 was accordingly produced.

In the constitution of shaft 2, the polyamide elastomer as a resin for the first outer layer 11 was used to coat or cover all zones of the proximal zone 3 to the distal zone 5.

(2) The above shaft tube was connected to a power injector, and a saline solution was injected to evaluate the shaft tube for its injection-admissible maximum pressure $P_{max}$ (psi(lb/in$^2$)) and a flow rate $FR_{max}$ (ml/sec.). A set injection speed of 10 ml/second and a set injection amount of 10 ml were employed. Table 2 shows the results.

Comparative Example 2

A shaft tube 2 that was formed of a multilayered tube for a microcatheter and that had a layer structure shown in Table 1 was produced as follows.

Sixteen stainless steel wires having a diameter of 0.03 mm each were braided on a PTFE tube that was employed for an inner layer 8 and that had a resin thickness of 0.006 mm and an internal diameter of 0.56 mm, to coat or cover the outer surface thereof. A first outer layer 11, a second outer layer 12 and a third outer layer 13 were formed thereon by a simultaneous multilayer melt-extrusion with a multilayer extrusion molding machine having a ring die.

A polyamide elastomer (hardness 35 D) was used as a resin for the first outer layer 11, a polyamide elastomer (hardness 63 D), as a resin for the second outer layer 12, and nylon 12 (hardness 77 D), as a resin for the third outer layer 13. The shaft tube 2 having a distal zone 5 with an outer diameter of 0.73 mm, an intermediate zone 4 with an outer diameter of 0.85 mm and a proximal zone 3 with an outer diameter of 0.93 was accordingly produced.

In the constitution of shaft 2, the resin for the first outer layer 11 was used for coating the distal zone 5 alone.

(2) The above shaft tube was connected to a power injector, and a saline solution was injected to evaluate the shaft tube for its injection-admissible maximum pressure $P_{max}$ (psi(lb/in$^2$)) and a flow rate $FR_{max}$ (ml/sec.) A set injection speed of 10 ml/second and a set injection amount of 10 ml were employed. Table 2 shows the results.

Example 2

A shaft tube 2 that was formed of a multilayered tube for a microcatheter and that had a layer structure shown in Table 1 was produced as follows.

Sixteen stainless steel wires having a diameter of 0.03 mm each were braided on a PTFE tube that was employed for an inner layer 8 and that had a resin thickness of 0.006 mm and an internal diameter of 0.56 mm, to coat or cover the outer surface thereof. A first outer layer 11, a second outer layer 12 and a third outer layer 13 were formed thereon by a simultaneous multilayer melt-extrusion with a multilayer extrusion molding machine having a ring die.

A polyamide elastomer (hardness 35 D) was used as a resin for the first outer layer 11, a polyamide elastomer (hardness 63 D), as a resin for the second outer layer 12, and nylon 12 (hardness 77 D), as a resin for the third outer layer 13. The shaft tube having a distal zone 5 with an outer diameter of 0.73 mm, an intermediate zone 4 with an outer diameter of 0.85 mm and a proximal zone 3 with an outer diameter of 0.93 was accordingly produced.

In the constitution of shaft 2, the resin for the first outer layer 11 was used to coat or cover all zones of the proximal zone 3 to the distal zone 5.

(2) The above shaft tube was connected to a power injector, and a saline solution was injected to evaluate the shaft tube for its injection-admissible maximum pressure $P_{max}$ (psi(lb/in$^2$)) and an $FR_{max}$ flow rate (ml/sec.) under the above pressure. A set injection speed of 10 ml/second and a set injection amount of 10 ml were employed. Table 2 shows the results.

TABLE 1

| | Inner layer 8 | Braid (reinforcing material) | | Forward end portion (distal zone) 5 Resin (Shore hardness: D) | Forward end portion (distal zone) 5 Outer diameter (mm) | Inter-mediate zone 4 Resin (Shore hardness: D) | Inter-mediate zone 4 Outer diameter (mm) | Base end portion (proximal zone) 3 Resin (Shore hardness: D) | Base end portion (proximal zone) 3 Outer diameter (mm) |
|---|---|---|---|---|---|---|---|---|---|
| C Ex. 1 | PE | SUS 304 | First outer layer | 55 D | 0.73 | Nil | 0.93 | Nil | 0.93 |
| | | | Second outer layer | Nil | | 63 D | | Nil | |
| | | | Third outer layer | Nil | | Nil | | 77 D | |
| Ex. 1 | PE | SUS 304 | First outer | 55 D | 0.73 | 55 D | 0.93 | 55 D | 0.93 |

TABLE 1-continued

| | Inner layer 8 | Braid (reinforcing material) | | Forward end portion (distal zone) 5 | | Inter-mediate zone 4 | | Base end portion (proximal zone) 3 | |
|---|---|---|---|---|---|---|---|---|---|
| | | | | Resin (Shore hardness: D) | Outer diameter (mm) | Resin (Shore hardness: D) | Outer diameter (mm) | Resin (Shore hardness: D) | Outer diameter (mm) |
| | | | Second outer layer | Nil | | 63 D | | Nil | |
| | | | Third outer layer | Nil | | Nil | | 77 D | |
| C Ex. 2 | PTFE | SUS 304 | First outer layer | 35 D | 0.73 | Nil | 0.85 | Nil | 0.93 |
| | | | Second outer layer | Nil | | 63 D | | Nil | |
| | | | Third outer layer | Nil | | Nil | | 77 D | |
| Ex. 2 | PTFE | SUS 304 | First outer layer | 35 D | 0.73 | 35 D | 0.85 | 35 D | 0.93 |
| | | | Second outer layer | Nil | | 63 D | | Nil | |
| | | | Third outer layer | Nil | | Nil | | 77 D | |

Ex. = Example,
C Ex. = Comparative Example

TABLE 2

| | Maximum injection pressure ($P_{max}$) | Flow rate ($FR_{max}$) |
|---|---|---|
| CEx. 1 | 100 psi or less | Leaked at 100 psi. |
| Ex. 1 | 1200 psi | 4.8 ml/sec |
| CEx. 2 | 100 psi or less | Leaked at 100 psi. |
| Ex. 2 | 1200 psi | 4.8 ml/sec |

Ex. = Example, CEx. = Comparative Example (Observation of Results)

As is clear from Table 2, the microcatheters of Examples 1 and 2 in which the first outer layer 11 resin was coated or shrouded on all the zones of the proximal zone 3 to the distal zone 5 exhibited a maximum injection pressure of 1,200 psi or high pressure resistance since the adhesion between the reinforcing material (braid) 7 and the outer layer was secured in the entire region. On the other hand, the tubes of Comparative Examples 1 and 2 in which the first outer layer 11 was coated on the distal zone 5 alone caused a leaking at as low as 100 psi. This is assumed to be caused by poor adhesion between the reinforcing material (braid) 7 and the outer layer.

INDUSTRIAL APPLICABILITY

The microcatheter of this invention is improved in pressure resistance and improved in anti-kinking property, so that it is made possible to approach a minute blood vessel superselectively, and thus enabling it to practice imaging of a blood vessel, administration of dosage, or treatment of embolus, etc., superselectively. Thus, the microcatheter of this invention has very high industrial applicability.

The invention claimed is:

1. A microcatheter comprising:
    a flexible shaft tube extending from a proximal end to a distal end and connected to a connector, the shaft tube being sectioned into, and composed of, a proximal zone, a middle zone and a distal zone in this order in the longitudinal direction from the connector to the forward end thereof, each zone being formed of a multilayered tube, and the shaft tube including three types of multilayered tubes different in hardness,
    which comprises:
    (i) an inner layer extending along all the zones from the proximal zone, through the middle zone, to the distal zone of the shaft tube, and a reinforcing material being fitted to the outer circumference of said inner layer,
    (ii) a first outer layer extending along all the zones from the proximal zone, through the middle zone, to the distal zone of the shaft tube so as to coat or cover, and adhere to, the inner layer and the reinforcing material, to form a basic layer structure (BLS) composed of the inner layer/reinforcing material/first outer layer, forming generally a 2-layered structure of the first outer layer/reinforced inner layer, in the distal zone of the shaft tube,
    (iii) a second outer layer coating the first outer layer of the basic layer structure (BLS), forming generally a 3-layered structure of the second outer layer/first outer layer/reinforced inner layer, in the middle zone of the shaft tube, and
    (iv) a third outer layer coating the first outer layer of the basic layer structure (BLS), forming generally a 3-layered structure of the third outer layer/first outer layer/reinforced inner layer, in the proximal zone of the shaft tube, and (I) wherein said 3-layered middle zone is positioned between the 3-layered proximal zone and the 2-layered distal zone such that a first end of the middle zone directly contacts the proximal zone and a second opposite end of the middle zone directly contacts the distal zone, and such that the middle zone occupies a clearly-identifiable or distinguishable portion from the proximal zone and the distal zone, and wherein the proximal zone extends from the middle zone to the proximal end of the shaft tube, and within each of the proximal zone, the middle zone, and the distal zone of the shaft, hardness and layer-thickness is kept substantially the same for each zone, and (II) wherein said second outer layer covers substantially an entire length of the middle zone with its constant-thicknessed layer, thereby protecting the middle zone of the shaft tube, and (III) wherein the second outer layer (constant hardness: H(2)m) in the 3-layered middle zone has a different hardness from that of the third outer layer (constant hardness: H(3)p) of the 3-layered proximal zone, and the second outer layer (constant hardness: H(2)m) in the 3-layered middle zone is composed of a same or chemically same material as the first and third outer layers, in which the second outer layer forming material of the 3-layered middle zone is softer than that of the third outer layer (constant hardness: H(3)p) of the 3-layered proximal zone and harder than that of the first outer layer (constant hardness: H(1)d) of the 2-layered distal zone, and (IV) wherein the first outer layer of the basic layer structure (BLS) has the same hardness throughout the proximal zone (constant hardness: H(1)P), the middle zone (constant hardness: H(1)m), and the distal zone (constant hardness: H(1)d), wherein H(3)p, H(2)m, H(1)d, H(1)P, H(1)m, and H(1)d have relationships (a), (b):

(a) H(3)p>H(2)m>H(1)d, and (b) H(1)p=H(1)m=H(1)d.

2. The microcatheter recited in claim 1, wherein the first outer layer has a thickness of 0.03 mm or less.

3. The microcatheter recited in claim 1, wherein the second outer layer covers substantially an entire length of the middle zone with its constant-thicknessed and constant-hardnessed layer, thereby protecting the middle zone of the shaft tube.

4. A microcatheter comprising:

a flexible shaft tube extending from a proximal end to a distal end and connected to a connector, the shaft tube being sectioned into, and composed of, a proximal zone, a middle zone and a distal zone in this order in the longitudinal direction from the connector to the forward end thereof, each zone being formed of a multilayered tube, and the shaft tube including three types of multilayered tubes different in hardness, which comprises:

(i) the proximal zone including an inner layer and a first outer layer formed on the outer circumference thereof, and the first outer layer including a reinforcing material fitted to the outer circumference of the inner layer, the reinforcing material is coated on the outer circumference of the inner layer, forming a reinforced inner layer, and a third outer layer coating the outer circumference of the first outer layer, forming generally a 3-layered structure of the third outer layer/first outer layer/reinforced inner layer, (ii) the middle zone being composed of the inner layer and the first outer layer, the first outer layer having the reinforcing material fitted to the outer circumference of the inner layer forming the reinforced inner layer, the reinforcing material coating on the outer circumference of the inner layer and a second outer layer coating the outer circumference of the first outer layer including the reinforce material, forming generally a 3-layered structure of the second outer layer/first outer layer/reinforced inner layer, (iii) the distal zone including the inner layer and the first outer layer, the first outer layer having the reinforcing material fitted to the outer circumference of the inner layer, and the first outer layer coating the outer circumference of the reinforcing material, forming generally a 2-layered structure of the first outer layer/reinforced inner layer, and (iv) the first outer layer coating the reinforcing material and the inner layer so as to extend along all of the proximal zone, through the middle zone, to the distal zone of the shaft tube, the basic layer structure (BLS) being composed of the inner layer/reinforcing material/first outer layer, and (I) wherein said 3-layered middle zone is positioned between the 3-layered proximal zone and the 2-layered distal zone such that a first end of the middle zone directly contacts the proximal zone and a second opposite end of the middle zone directly contacts the distal zone, and such that the middle zone occupies a clearly-identifiable or distinguishable portion from the proximal zone and the distal zone, and wherein the proximal zone extends from the middle zone to the proximal end of the shaft tube, and within each of the proximal zone, the middle zone, and the distal zone of the shaft, hardness and layer-thickness is kept substantially the same for each zone, and (II) wherein said second outer layer covers substantially an entire length of the middle zone with its constant-thicknessed layer, thereby protecting the middle zone of the shaft tube, and (III) wherein, in the 3-layered middle zone, the second outer layer (constant hardness: H(2)m) coating the outer circumference of the first outer layer (constant hardness: H(1)m) has a different hardness from that of the third outer layer (constant hardness: H(3)p) of the 3-layered proximal zone, and (IV) wherein the second outer layer in the 3-layered middle zone (constant hardness: H(2)m) is composed of a same or chemically same material as the first and third outer layers, in which the second outer layer (constant hardness: H(2)m) forming material of the 3-layered middle zone is softer than that of the third outer layer (constant hardness: H(3)p) of the 3-layered proximal zone and harder than that of the first outer layer (constant hardness: H(1)d) of the 2-layered distal zone, and (V) wherein the first outer layer of the basic layer structure (BLS) has the same hardness throughout the proximal zone (H(1)P), the middle zone (H(1)m), and the distal zone (H(1)d), wherein H(3)p, H(2)m, H(1)d, H(1)P, H(1)m, and H(1)d have relationships (a), (b):

(a) H(3)p>H(2)m>H(1)d, and (b) H(1)p=H(1)m=H(1)d.

5. The microcatheter recited in claim 4, wherein the first outer layer has a thickness of 0.03 mm or less.

6. The microcatheter recited in claim 4, wherein the second outer layer covers substantially an entire length of the middle zone with its constant-thicknessed and constant-hardnessed layer, thereby protecting the middle zone of the shaft tube.

7. A microcatheter comprising:

a flexible shaft tube extending from a proximal end to a distal end and connected to a connector, the shaft tube being sectioned into, and composed of, a proximal zone, a middle zone and a distal zone in this order in the longitudinal direction from the connector to the forward end thereof, each zone being formed of a multilayered tube, and the shaft tube including three types of multilayered tubes different in hardness, which comprises:

(i) an inner layer extending along all the zones from the proximal zone, through the middle zone, to the distal zone of the shaft tube, and a reinforcing material being fitted to the outer circumference of said inner layer, (ii) a first outer layer extending along all the zones from the proximal zone, through the middle zone, to the distal zone of the shaft tube so as to coat or cover, and adhere to, the inner layer and the reinforcing material, to form a basic layer structure (BLS) composed of the inner layer/reinforcing material/first outer layer, forming generally a 2-layered structure of the first outer layer/reinforced inner layer, in the distal zone of the shaft tube, (iii) a second outer layer coating the first outer layer of the basic layer structure (BLS), forming generally a 3-layered structure of the second outer layer/first outer layer/reinforced inner layer, in the middle zone of the shaft tube, and not coating the first outer layer in the proximal and distal zones, and (iv) a third outer layer coating the first outer layer of the basic layer structure (BLS), forming generally a 3-layered structure of the third outer layer/first outer layer/reinforced inner layer, in the proximal zone of the shaft tube, and not coating the first outer layer in the middle and distal zones, and (v) both ends of the 3-layered middle zone are connected to the 2-layered distal zone and 3-layered proximal zone respectively, (I) wherein said second outer layer covers substantially an entire length of the middle zone with its constant-thicknessed layer, thereby protecting the middle zone of the shaft tube, and such that a first end of the middle zone directly contacts the proximal zone and a second opposite end of the middle zone directly contacts the distal zone, and wherein the proximal zone extends from the middle zone to the proximal end of the shaft tube, (II) wherein, the second outer layer (constant hardness: $H(2)m$) in the 3-layered middle zone has a different hardness from that of the third outer layer (constant hardness: $H(3)p$) of the 3-layered proximal zone, and the second outer layer (constant hardness: $H(2)m$) in the 3-layered middle zone is composed of a same or chemically same material as the first (constant hardness: $H(1)m$) and third outer layers (constant hardness: $H(3)m$), in which the second outer layer forming material is softer than that of the third outer layer and harder than that of the first outer layer, and (III) the first outer layer of the basic layer structure (BLS) has the same hardness throughout the proximal zone ($H(1)P$), middle zone ($H(1)m$), and distal zone ($H(1)d$), wherein $H(3)p$, $H(2)m$, $H(1)d$, $H(1)P$, $H(1)m$, and $H(1)d$ have relationships (a), (b):

(a) $H(3)p > H(2)m > H(1)d$, and (b) $H(1)p = H(1)m = H(1)d$.

8. The microcatheter recited in claim 7, wherein said 3-layered middle zone occupies clearly-identifiable or distinguishable portion from the proximal zone and the distal zone, and within each of the proximal zone, the middle zone, and the distal zone of the shaft, hardness and layer-thickness is kept substantially the same for each zone.

9. The microcatheter recited in claim 7, wherein the first outer layer has a thickness of 0.03 mm or less.

10. The microcatheter recited in claim 7, wherein the second outer layer covers substantially an entire length of the middle zone with its constant-thicknessed and constant-hardnessed layer, thereby protecting the middle zone of the shaft tube.

11. A microcatheter comprising:

a flexible shaft tube extending from a proximal end to a distal end and connected to a connector, the shaft tube being sectioned into, and composed of, a proximal zone, a middle zone and a distal zone in this order in the longitudinal direction from the connector to the forward end thereof, each zone being formed of a multilayered tube, and the shaft tube including three types of multilayered tubes different in hardness, which comprises:

(i) the proximal zone including an inner layer and a first outer layer formed on the outer circumference thereof, and the first outer layer including a reinforcing material fitted to the outer circumference of the inner layer, the reinforcing material is coated on the outer circumference of the inner layer thus forming a reinforced inner layer, and a third outer layer coating the outer circumference of the first outer layer and not coating the first outer layer in the middle and distal zones, forming generally a 3-layered structure of the third outer layer/first outer layer/reinforced inner layer, (ii) the middle zone being composed of the inner layer and the first outer layer, the first outer layer having the reinforcing material fitted to the outer circumference of the inner layer, thus forming the reinforced inner layer, the reinforcing material coating on the outer circumference of the inner layer and a second outer layer coating the outer circumference of the first outer layer including the reinforce material and not coating the first outer layer in the proximal and distal zones, forming generally a 3-layered structure of the second outer layer/first outer layer/reinforced inner layer, (iii) the distal zone including the inner layer and the first outer layer, the first outer layer having the reinforcing material fitted to the outer circumference of the inner layer, and the first outer layer coating the outer circumference of the reinforcing material, forming a 2-layered structure of the first outer layer/reinforced inner layer to form a basic layer structure (BLS), the distal zone formed from only the 2-layered BLS structure without a further outer layer, and (iv) the first outer layer coating the reinforcing material and the inner layer so as to extend along all of the proximal zone, through the middle zone, to the distal zone of the shaft tube, the basic layer structure (BLS) being composed of the inner layer/reinforcing material/first outer layer, and (v) both ends of the 3-layered middle zone are connected to the 2-layered distal zone and 3-layered proximal zone respectively, (I) wherein said second outer layer covers substantially an entire length of the middle zone with its constant-thicknessed layer, thereby protecting the middle zone of the shaft tube, and such that a first end of the middle zone directly contacts the proximal zone and a second opposite end of the middle zone directly contacts the distal zone, and wherein the proximal zone extends from the middle zone to the proximal end of the shaft tube, (II) wherein, in the 3-layered middle zone, the second outer layer (constant hardness: H(2)m) coating the outer circumference of the first outer layer (constant hardness: H(1)m) has a different hardness from that of the third outer layer (constant hardness: H(3)p) of the 3-layered proximal zone, and the second outer layer (constant hardness: H(2)m) in the 3-layered middle zone is composed of a same or chemically same material as the first and third outer layers, in which the second outer layer (constant hardness: H(2)m) forming material is softer than that of the third outer layer (constant hardness: H(3)p) of the 3-layered proximal zone and harder than that of the first outer layer (constant hardness: H(1)d) of the 2-layered distal zone and (III) wherein the first outer layer of the basic layer structure (BLS) has the same hardness throughout the proximal zone (constant hardness: H(1)p), middle zone (constant hardness: H(1)m), and distal zone (constant hardness: H(1)d), wherein H(3)p, H(2)m, H(1)d), H(1)P, H(1)m, and H(1)d have relationships (a), (b):

(a) H(3)p>H(2)m>H(1)d, and (b) H(1)p=H(1)m=H(1)d.

12. The microcatheter recited in claim 11, wherein said 3-layered middle zone occupies a clearly-identifiable or distinguishable portion from the proximal zone and the distal zone, and within each of the proximal zone, the middle zone, and the distal zone of the shaft, hardness and layer-thickness is kept substantially the same for each zone.

13. The microcatheter recited in claim 11, wherein the first outer layer has a thickness of 0.03 mm or less.

14. The microcatheter recited in claim 11, wherein the second outer layer covers substantially an entire length of the middle zone with its constant-thicknessed and constant-hardnessed layer, thereby protecting the middle zone of the shaft tube.

* * * * *